(12) United States Patent
Harrell, Jr.

(10) Patent No.: US 7,168,327 B2
(45) Date of Patent: Jan. 30, 2007

(54) METHOD OF PREDICTION OF IN-VIVO POLYMER PERFORMANCE BY EXTERNAL EXPERIMENTATION

(76) Inventor: E. Ray Harrell, Jr., 32097 Bexley Cir., Avon Lake, OH (US) 44012

(*) Notice: Subject to any disclaimer, the term of this patent is extended or adjusted under 35 U.S.C. 154(b) by 469 days.

(21) Appl. No.: 10/828,976

(22) Filed: Apr. 21, 2004

(65) Prior Publication Data

US 2004/0215403 A1  Oct. 28, 2004

Related U.S. Application Data

(60) Provisional application No. 60/465,975, filed on Apr. 28, 2003.

(51) Int. Cl.
*G01D 1/00* (2006.01)

(52) U.S. Cl. ...................................................... 73/787

(58) Field of Classification Search .................. 73/787
See application file for complete search history.

(56) References Cited

U.S. PATENT DOCUMENTS

| | | | |
|---|---|---|---|
| 4,033,181 A | 7/1977 | Oeser | 73/800 |
| 4,567,774 A * | 2/1986 | Manahan et al. | 73/826 |
| 4,768,383 A * | 9/1988 | Koyama et al. | 73/787 |
| 4,855,170 A | 8/1989 | Darvell et al. | 428/40.2 |
| 4,907,457 A * | 3/1990 | Nishimura et al. | 73/787 |
| 5,349,870 A | 9/1994 | Webber et al. | 73/808 |
| 5,792,525 A | 8/1998 | Fuhr et al. | 428/35.7 |
| 6,581,473 B2 | 6/2003 | Takahara et al. | 73/788 |
| 6,810,748 B1 * | 11/2004 | Nishida et al. | 73/788 |

OTHER PUBLICATIONS

Enker et al. "Artificial Disc Replacement" *SPINE*, vol. 18, No. 8, pp. 1061-1070 (1993).

* cited by examiner

*Primary Examiner*—Michael Cygan
*Assistant Examiner*—O. Davis
(74) *Attorney, Agent, or Firm*—John H. Hornickel

(57) ABSTRACT

A method is disclosed of using external polymeric analytical techniques to predict in-vivo polymeric performance, more particularly, viscoelastic property characterization for performance modeling of biomedical devices that incorporate a polymeric component and are load-bearing during service. Time-Temperature Superposition can be used to accelerate external testing of pertinent properties. Boltzmann's superposition provides a mathematical methodology for determining the time-dependent strain that develops in response to an imposed stress history. The modeling of the present invention provides an opportunity to describe and predict behavior of the device during in-vivo service, as well as it providing a basis for evaluating alternate "candidate" polymers for use in the construction of the device.

1 Claim, 11 Drawing Sheets

Fatigue S-N Failure Curve

Compressive Creep Sample Geometry

"Fixed" Boundary    "Lubricated" Boundary $\varepsilon = \Delta h/H_0$ ; $\sigma$ = Load/Area $\varepsilon(t) = D(t)\sigma$ Creep/Creep Recovery--Single Load Cycle $\varepsilon(t) = \sigma_1 D(t)$  Creep Phase $\varepsilon(t) = \sigma_1 D(t) - \sigma_1 D(t-t_r)$  Recovery Phase

METHOD OF PREDICTION OF IN-VIVO POLYMER PERFORMANCE BY EXTERNAL EXPERIMENTATION

CLAIM OF PRIORITY

This application claims priority from U.S. Provisional Patent Application Ser. No. 60/465,975 bearing Attorney Docket Number 12003007 and filed on Apr. 28, 2003.

FIELD OF THE INVENTION

This invention relates to using external polymeric analytical techniques to predict in-vivo polymeric performance.

BACKGROUND OF THE INVENTION

Polymers have transformed material science in the past seventy years. Medical science has benefited from the rheology and morphology of polymers for the construction of prosthetic medical devices and implants.

Any medical device for mammalian usage requires extensive screening of performance to assure safety and efficacy of use. Stages of clinical trials proceeds from animal patients to human patients. The opportunity cost of such clinical trials is significant in terms of risk, expense, and time.

SUMMARY OF THE INVENTION

The art needs a means to limit the effort of clinical trials for polymer performance in medical devices.

The present invention solves that problem by providing a method of using external polymeric analytical techniques to predict in-vivo polymeric performance.

"External" means beyond the mammalian body. "In-vivo" means within the mammalian body.

"Polymeric" means of or relating to "polymers", which can be naturally-occurring polymers, synthetically-produced polymers, combinations of naturally-occurring polymers and synthetically-produced polymers by physical or chemical interaction, or combinations thereof.

The ability to predict performance is extremely important in the development of in-vivo biomedical devices, such as implants for skeletal joints. Often the devices contain a polymeric component that provides damping as well as structural integrity. The devices are exposed to complex deformations (both shear and compression-extension) and complex loading schedules (cyclic loads of varying amplitude/magnitude).

Aside from bio-compatibility considerations, the lifetime of the polymeric component is typically determined by two characteristics of the polymeric component.

The first is accumulated, irreversible strains (micro-failures). Accumulated micro-failure is usually characterized by fatigue testing (lifetime vs. load or deformation amplitude).

The second "failure" mode involves the viscoelastic deformational response of the polymeric component to the loading schedule.

The present invention focuses on this second "failure" mode. Specifically, the present invention uses time-temperature superposition to define the stress- and time-dependent properties of a polymeric component, extending to 20 years of in-vivo usage, from predictions based on external laboratory measurements requiring only a few weeks. Boltzmann's superposition is used to define the deformation response to a cyclic loading schedule. Lifetime is assessed by the ability of the device to maintain a required geometry during the imposed loading schedule.

One aspect of the present invention is a method for predicting in-vivo polymer performance in a mammalian body via external experimentation, comprising the steps of:

(a) determining stress levels and the duration times of stress application, denominated a daily stress cycle that the polymeric component will be subjected to during mammalian body activities for the lifetime of the device;

(b) determining compressive creep and recoverable creep compliance at selected stresses, as determined in step (a), and temperatures to obtain master curves of compressive creep compliance that analytically define compressive creep strain as functions of time and stress;

(c) determining single creep/creep recovery strain curves for each mammalian body activity of step (a) calculated from the compressive creep compliance master curves of step (b), wherein a creep phase is interrelated to a recovery phase, to obtain a compressive creep model for a single stress cycle;

(d) determining a total residual strain after repeated stress cycles from the compressive creep model of step (c), to obtain a compressive creep model for the polymer subjected to repeated daily mammalian activities, denominated compressive stress cycles;

(e) computing maximum compressive strain curves from a compressive strain during an activity in relation to number of days of activity, wherein the number of days can range from a few days to several years; and (f) using the maximum compressive strain curves of step (e) to predict in-vivo performance of the polymer by calculating polymer deflection as a function of original geometry of the device to be made of the polymer.

A feature of the present invention is that the polymer need not be placed in-vivo without some estimation of its performance in-vivo.

An advantage of the present invention is that the external prediction can reduce patient risk, duration of clinical trial product screening activities, and attendant expenses associated with both.

The present invention can achieve the following goals:

1. Demonstrated Utility of Viscoelastic Property Characterization in Performance Modeling of Polymeric Biomaterials.

2. Time-Temperature Superposition Can Often Be Employed to Provide Long-Time Properties (Temperature-Acceleration).

3. Boltzmann's Superposition Provides Basis for Defining Stress/Strain Response for Various Loading Histories/Requirements.

4. Performance Modeling Can Provide Basis for Material Selection.

Other features and advantages will be revealed when amplifying on the embodiments of the invention in comparison with the following drawings.

EMBODIMENTS OF THE INVENTION

In-Vivo Polymer Predictive Performance

Polymers have found considerable popularity in biomedical applications because of their unique properties. Polymers possess both "solid-like" and "liquid-like" behavior. They can be used as "carriers" that change from a liquid to solid, depending on their environment. They can provide structural properties (rigidity) as well as energy dissipation (mechanical damping). They can provide friction reduction at moving surfaces.

Some of the biomedical applications that involve polymers include drug-delivery systems, dental adhesives, tissue adhesives, support fabric, prosthetic devices, skeletal implants, etc.

Each of these non-limiting in-vivo examples requires that the polymer provides the designed performance properties while being relatively inert to its surrounding, i.e. biocompatible.

The present invention uses viscoelastic property characterization to define the capability of a polymer to provide the "designed performance properties". (Bio-compatibility is not addressed.)

For example, one item benefiting from the present invention is a spinal implant device that replaces a damaged disc. The disc device contains a polymer that provides both structural integrity and mechanical damping. The in-vivo device is exposed to complex deformations involving both shear and compression-extension in response to a complex loading schedule, i.e. cyclic stresses that vary in magnitude and duration. The major "designed performance property" is that the device has to provide structural integrity in terms of extent of deformations for various loads for a lifetime of 30 years.

Lifetime predictions for "structural integrity" of a polymeric component are typically assessed by two techniques: cyclic fatigue and long-time creep. Fatigue studies emphasize failure by accumulated irreversible strains (micro-failures) or accumulated damage. Accelerated testing is accomplished by testing at cyclic stress levels that are higher than those involved in the application. Table 1 below summarizes this point.

TABLE 1

Survival Without Excessive Deformation

| Fatigue | Long-Time Creep |
|---|---|
| Cycles to Failure vs. Load | Viscoelastic Property Characterization |
| Accumulated Damage | Model Deformation vs. Time and Load History |
| Accelerated by Increasing Load | Accelerated by Increasing Temperature |
| Viscoelasticity | Irreversible Deformations |

Figure 1:
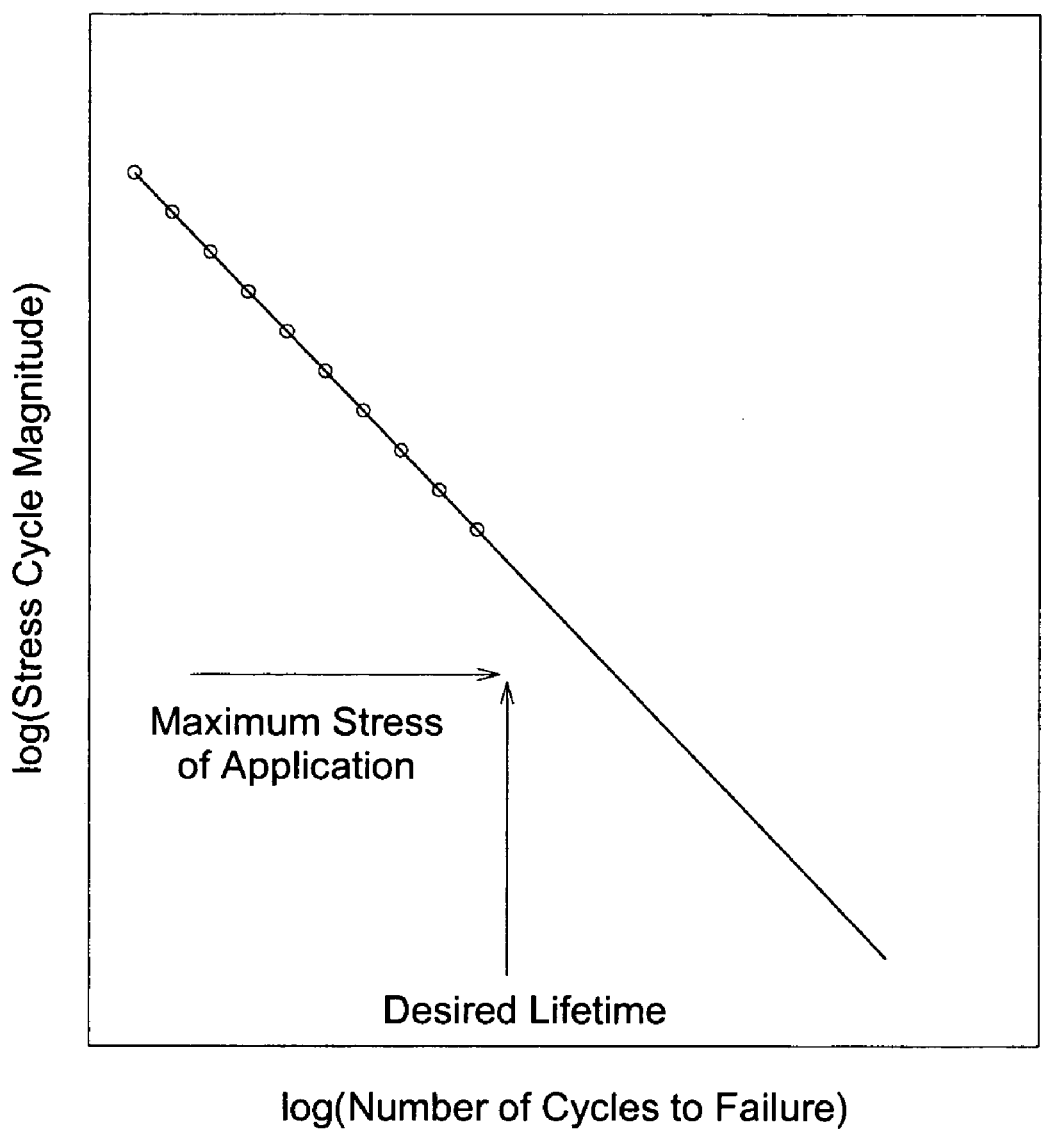
FIG. 1 shows a typical Fatigue S-N Failure Curve.

An S-N curve is obtained that describes the lifetime as a function of cyclic stress level. FIG. 1 shows a typical Fatigue S-N Failure Curve. If the polymer component "survives" the anticipated number of cycles that the device incurs during a 30-year lifetime at a cyclic stress level that exceeds the anticipated in-vivo stress, then the device is "acceptable". Although the S-N curve is generally interpreted in terms of accumulated damage, the change in cyclic deformation is also influenced by the viscoelasticity of the polymer component.

Returning to Table 1, long-time creep studies emphasize the viscoelastic properties of the polymer. Properties are measured to provide the capability to calculate/model the deformation of the polymeric component as functions of time and loading history for the projected lifetime of the device. Performance "acceptability" is directly related to deformation of the polymeric component throughout the proposed lifetime. Typically, creep and creep recovery experiments are performed at various constant stress levels to determine "linearity" of response. Irreversibility and non-linearity can be defined but accumulated damage is not part of the model. Acceleration of testing is accomplished by increasing the temperature of testing.

Figure 2:
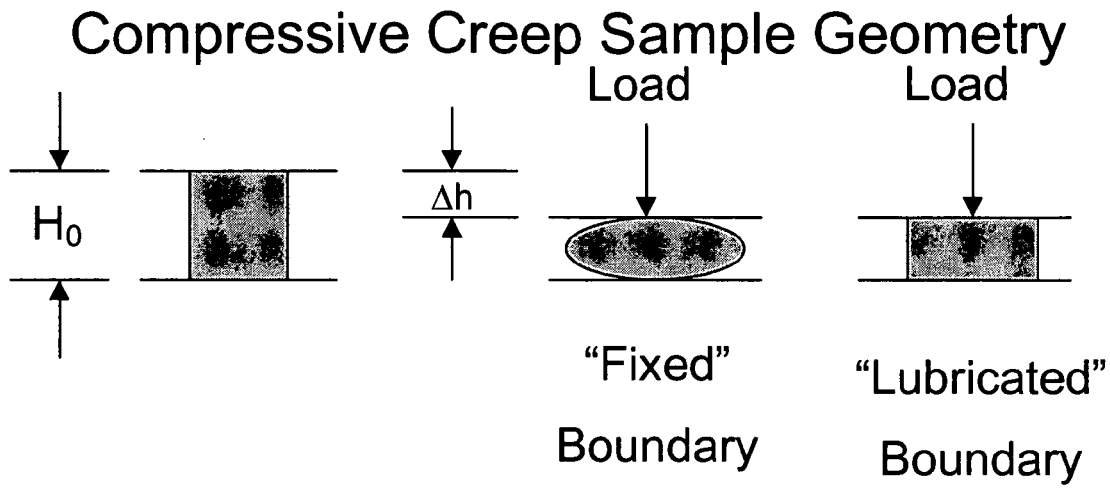
FIG. 2 shows a depiction of a sample geometry subjected to load.
Figure 3:
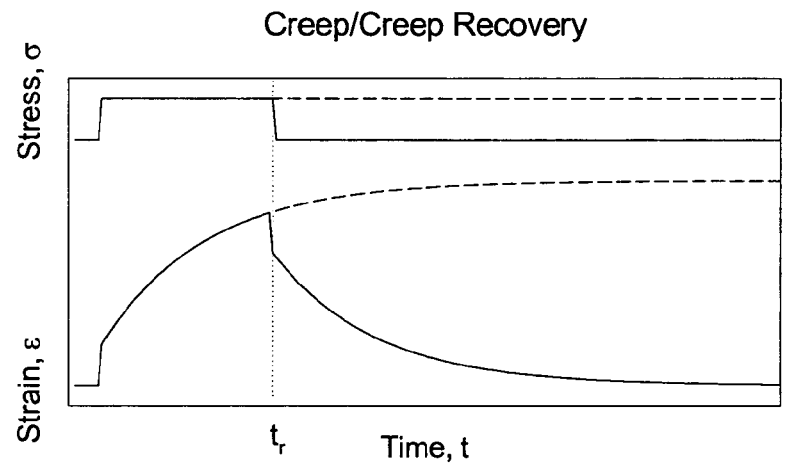
FIG. 3 shows a graph comparing stress and strain over time, showing creep and creep recovery.

FIG. 2 shows the geometry of the polymeric component in the disc device that will serve as the "model" for the device and for the compressive creep/creep recovery test. The cylindrical sample is confined at its top and bottom surfaces by an adhesive. The "fixed" boundary of the polymer causes a very complex stress/strain distribution throughout the sample (as can be shown by Finite Element Analysis, a technique known to those skilled in the art) compared with the essentially bi-axial strain that evolves from the "lubricated" boundary compressive creep test specimen. As shown in FIG. 2, a constant compressive stress (load divided by cross-sectional area) is applied to the sample at time zero and the time-dependent strain ($\Delta h$ divided by initial height, H, or thickness of the sample) is measured. At some time $t_r$ the stress is removed from the sample and the time-dependent strain (creep recovery) is measured. FIG. 3 shows that time-dependent response graphically.

Table 2 shows five equations concerning creep compliance and viscoelastic performance of the polymeric material.

TABLE 2

I $D(t) = \epsilon(t)/\sigma$ Creep Compliance
II $D = D(t)$ only; "Linear" Viscoelastic
III $D = D(t, \sigma)$ "Non-linear" Viscoelastic
IV $D_{creep} = D_{creeprecovery}$ "Reversible"
V $D_{creep} > D_{creeprecovery}$ "Non-reversible"

The compressive creep compliance, D(t), is defined as the ratio of the time-dependent strain divided by the constant stress. If D(t) is independent of stress, then the behavior of the polymer is classified as "linear" viscoelastic. If D(t) depends upon stress, then the behavior is classified as "non-linear" viscoelastic. The creep recovery portion of the experiment allows the calculation of a recoverable creep compliance, $D_r(t)$. If $D_r(t)$ is equal to D(t), then the deformation is considered to be "reversible". If $D_r(t)$ is less than D(t), then the deformation is considered to be "irreversible". "Irreversibility" can originate from a micro-fracture or from a purely viscous response.

Figure 4:
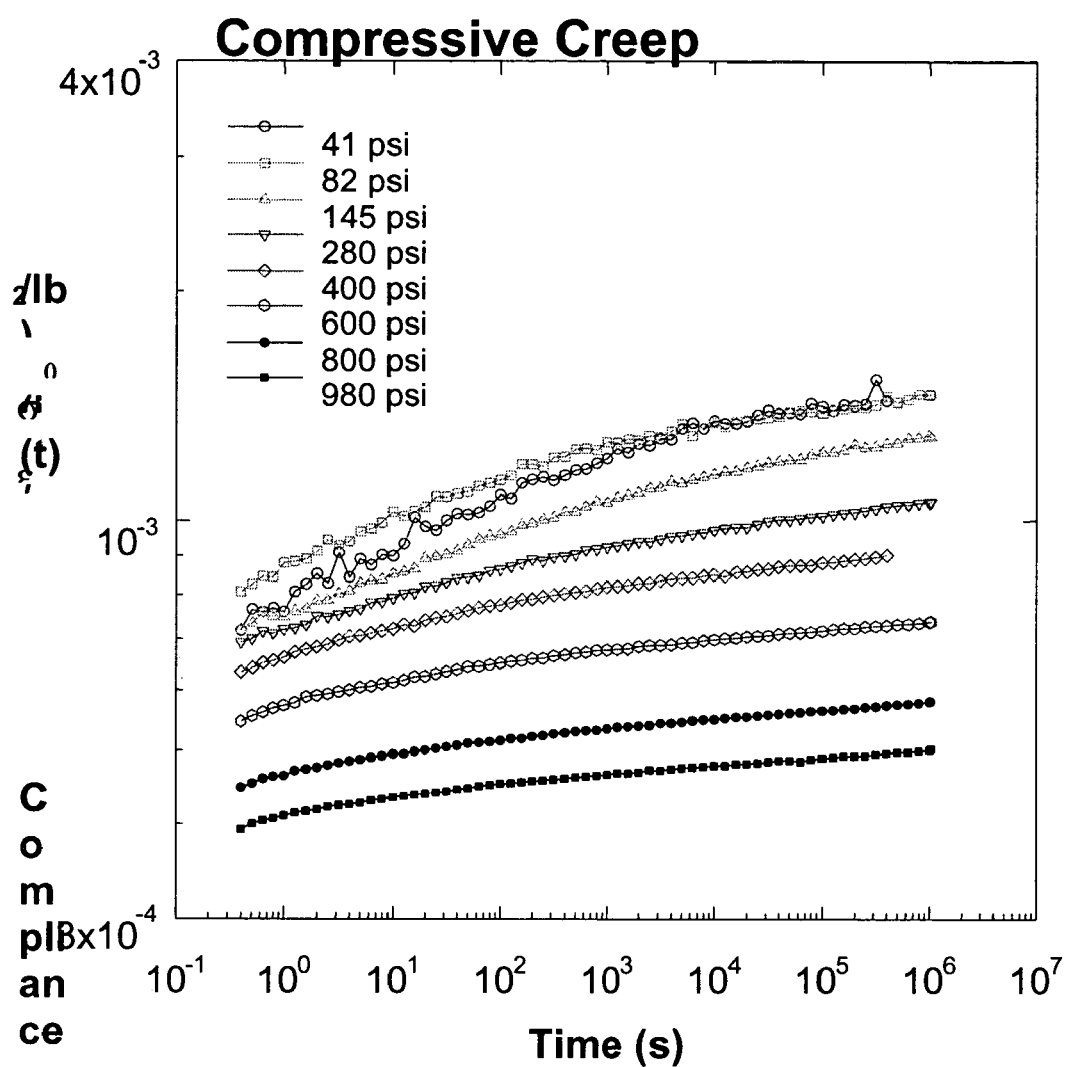
FIG. 4 displays the creep compliance for various compressive stresses (loads) for the polymeric component.

FIG. 4 displays the creep compliance for various compressive stresses (loads) for the polymeric component. As noted, the compliance is dependent on stress and is thus considered "non-linear". As applied stress increases the compliance decreases. Specifically, strain increases less than proportionally with increasing stress, i.e. the polymeric component "strain-hardens", which indicates the presence of a finite network structure. Each test required approximately 11.5 days at a test temperature of 37° C. Even though there is considerable information available within this creep compliance data, the 11.5 days of time is insufficient to use for predicting behavior to 30 years (10957 days or $9.5 \times 10^8$ s).

Time-Temperature Superposition is often used to develop a master curve of properties, such as creep compliance, for extrapolating to long-times. Increasing the testing temperature effectively accelerates the creep process so that it occurs in a shorter time-frame.

Figure 5:
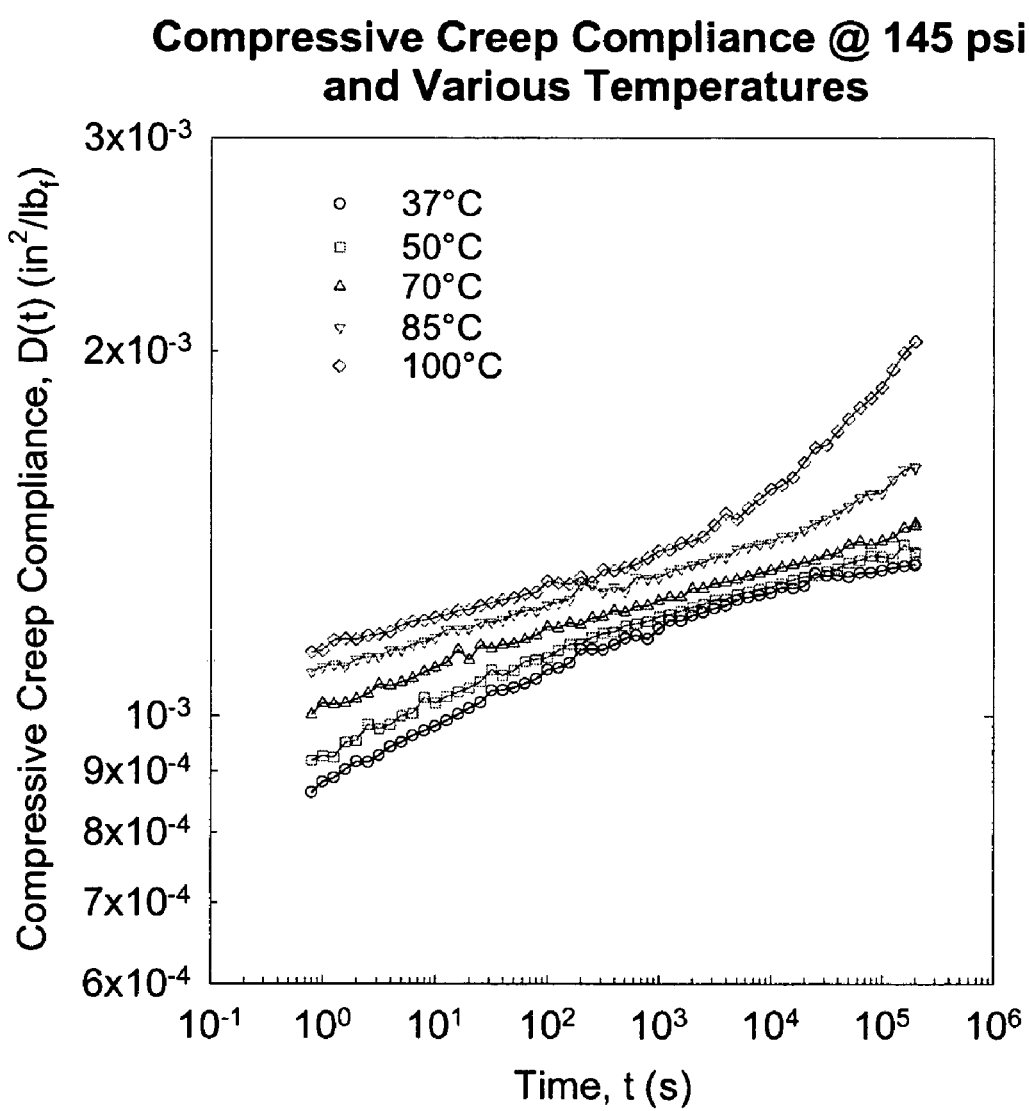
FIG. 5 displays creep compliance measurements that were obtained at a constant stress of 145 pounds per square inch (psi) at test temperatures of 37, 50, 70, 85 and 100° C.

FIG. 5 displays creep compliance measurements that were obtained at a constant stress of 145 psi at test temperatures of 37, 50, 70, 85 and 100° C. It is noteworthy that the compliance curves have regions of similar curvature and that compliance increases with increasing testing temperature. The acceleration of the creep process with increasing temperature allows one to shift each curve along the log-time scale to superpose with the data for the temperature of interest, i.e. for a temperature of 37° C.

Figure 6:
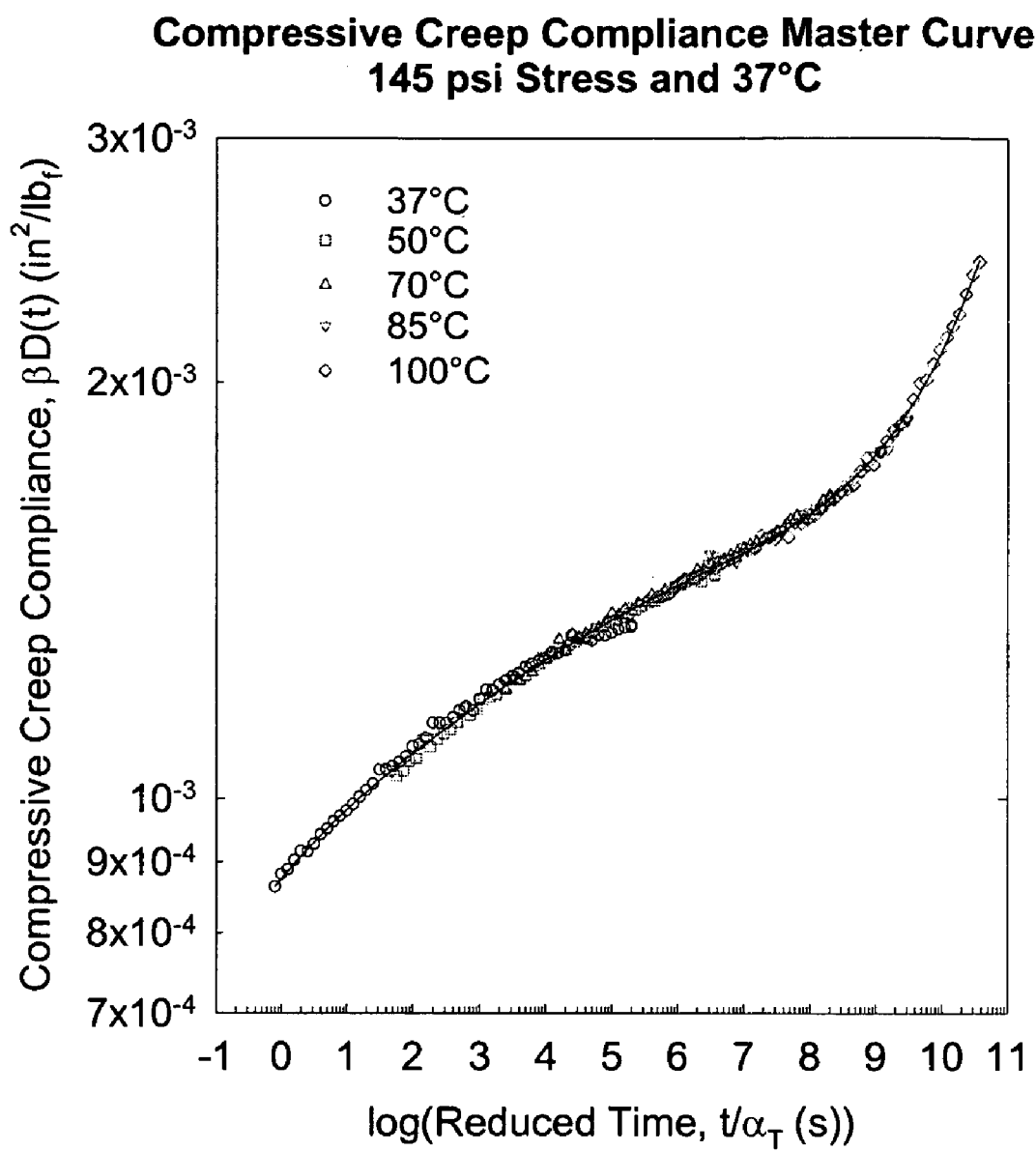
FIG. 6 shows a resulting master curve for the 37° C. creep compliance.

The resulting master curve for the 37° C. creep compliance is shown in FIG. 6. The use of Time-Temperature Superposition (temperature acceleration) provided creep compliance characterization at 37° C. for times in excess of $10^{10}$ s (300 years) from creep measurements at five temperatures involving creep times of only 55 hours for each test.

At this juncture, creep compliance of the polymeric component of the disc device has been determined as a function of compressive stress for times up to 30 years. This permits external prediction of in-vivo performance.

Time-dependence is provided by the 37° C. compliance master curves. Temperature-dependence (not necessary for the present application) is provided by the $\alpha_T$ function. Stress-dependence is provided by compliance master curves at the stresses of interest. The completion of the performance prediction model requires a knowledge of the loading schedule that is imposed on the device during the in-vivo lifetime.

Table 3 shows a typical daily load/stress schedule for the polymeric material in use.

TABLE 3

| Activity | Characteristic Stress (psi) | Daily Duration of Activity (hours) |
|---|---|---|
| Supine | 58 | 8.4 |
| Sit/Walk/Stand | 158 | 14 |
| Jumping/Playing | 238 | 1.5 |
| Bending/Lifting | 558 | 0.1 |

Although the device could be subjected to other than compressive stresses, the present discussion models only the deformational response to compressive stresses. As shown, the device is continuously subjected to a compressive stress of at least 58 psi throughout its lifetime. Each activity has an associated incremental increase in stress for a characteristic duration time.

(Certain liberties are taken to assign multiple types of activities to characteristic stress levels. The actual stress schedule will influence the deformational response but the trends that will be displayed by the present model will not be significantly affected.)

The modeling of the deformation of the device then uses Boltzmann's superposition as described in the equations shown in Equation VI below.

$$\epsilon(t) = \sigma_1 D(t-t_1) + \sigma_2 D(t-t_2) + \ldots + \sigma_n D(t-t_n)$$

where: $\sigma_i$=compressive stress (constant)
$t_i$=time of stress application
n=number of stress level changes Simply stated, the total deformational response of a polymer is equal to the sum of the individual strain responses for each incremental applied stress from the beginning of the loading/stress history and extending to the time of interest. Specifically, there is are deformational response contributions from the first stress application (first term) and each additional stress application that persist throughout the lifetime of the device.

Figure 7:
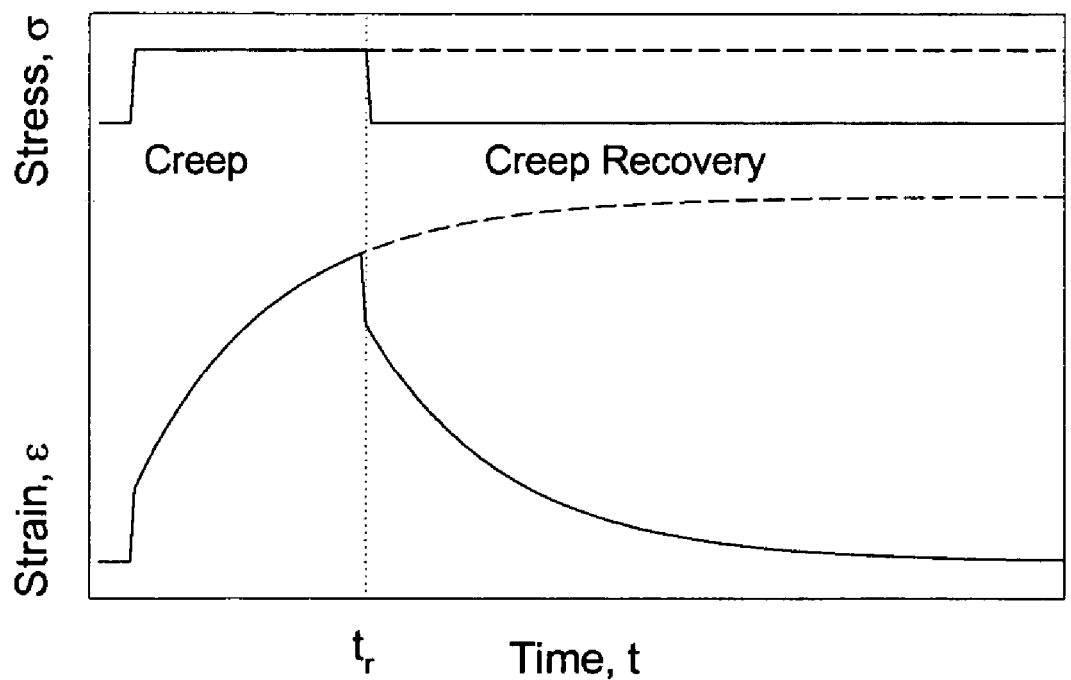
FIG. 7 depicts the strain response for a single stress cycle.

FIG. 7 depicts the strain response for a single stress cycle. Notice the persistence of a "residual" strain after removal of the stress. Mathematically, the time-dependent strain response from a single stress cycle can be represented by a two-term equation, as shown at the bottom of this slide. For a load/stress schedule having 3 daily stress cycles, the model describing time-dependent strain for 2 days involves 13 terms is shown in Table 4.

Non-linearity of the compressive creep model is introduced by selecting the appropriate master curve representation for compliance that is associated with the magnitude of the stress for the activity. The model describing time-dependent strain for a 30-year lifetime involves 65,746 terms, as seen in Table 4.

TABLE 4

Deformation Model: 4 Daily Activities; 2 Days

| | |
|---|---|
| $\epsilon(t) = \sigma_1 D_1(t)$ | Activity 1 (continuous) |
| $+\sigma_2 D_2(t - t_2) - \sigma_2 D_2(t - t_3)$ | Activity 2/Day 1 |
| $+\sigma_3 D_3(t - t_4) - \sigma_3 D_3(t - t_5)$ | Activity 3/Day 1 |
| $+\sigma_4 D_4(t - t_6) - \sigma_4 D_4(t - t_7)$ | Activity 4/Day 1 |
| $+\sigma_2 D_2(t - t_8) - \sigma_2 D_2(t - t_9)$ | Activity 2/Day 2 |
| $+\sigma_3 D_3(t - t_{10}) - \sigma_3 D_3(t - t_{11})$ | Activity 3/Day 2 |
| $+\sigma_4 D_4(t - t_{12}) - \sigma_4 D_4(t - t_{13})$ | Activity 4/Day 2 |
| ... | |
| For 30 year lifetime: $6 \times 365.25 \times 30 + 1$ | 65,746 terms! |

Figure 8:
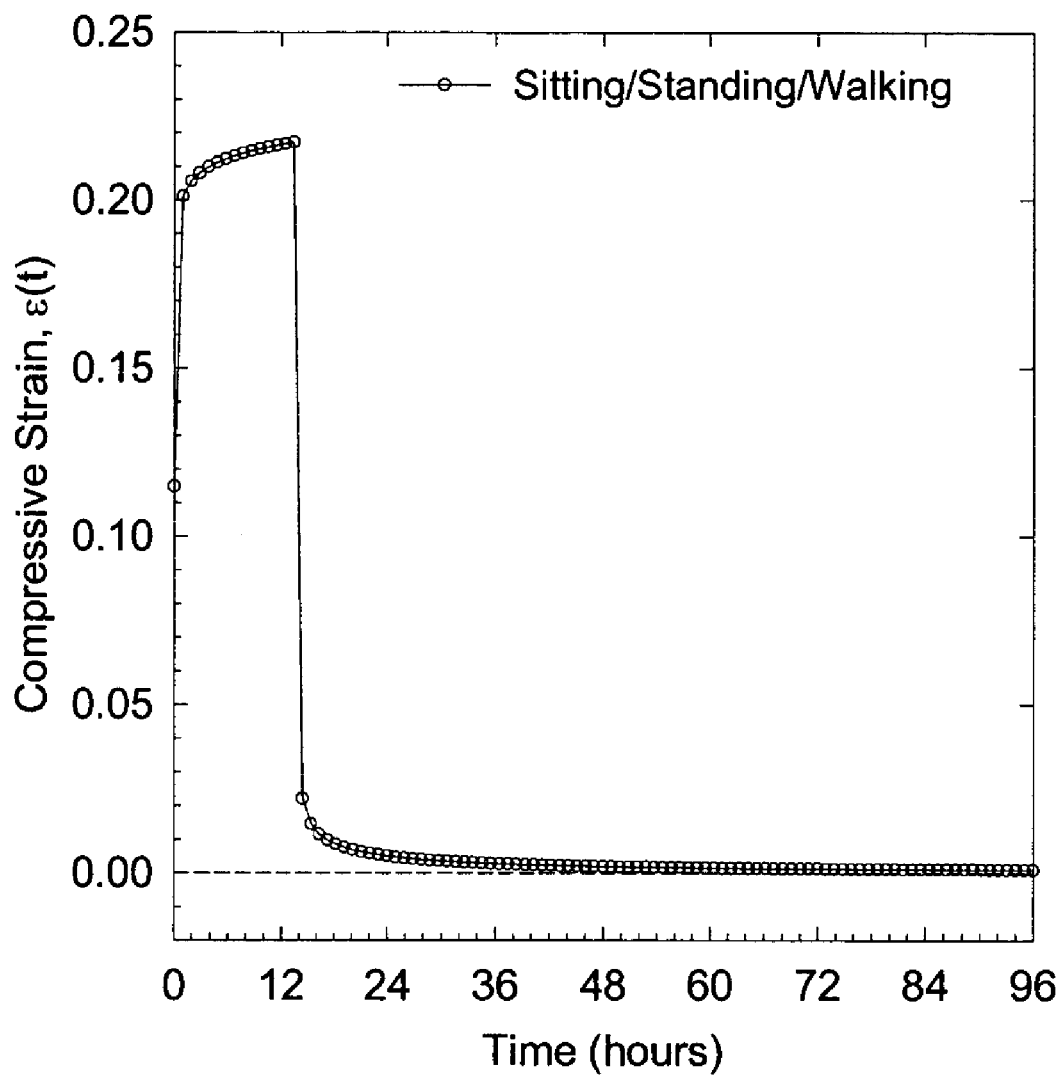
FIG. 8 is a graph of a compressive creep model for a single stress cycle of 158 psi.

Fortunately, and unexpectedly, the number of terms can be reduced to only 7 to provide an accurate description of the time-dependent strain. Consider the strain response to a single stress cycle, e.g. the Sitting/Walking/Standing activity as seen in FIG. 8. The strain for a daily stress cycle at day two is the sum the response at day two (creep recovery of day one stress cycle) and the response at day one (second stress cycle at day two). The strain at day three would be the sum of the responses at day one and at day two and at day three. And so on.

Figure 9:
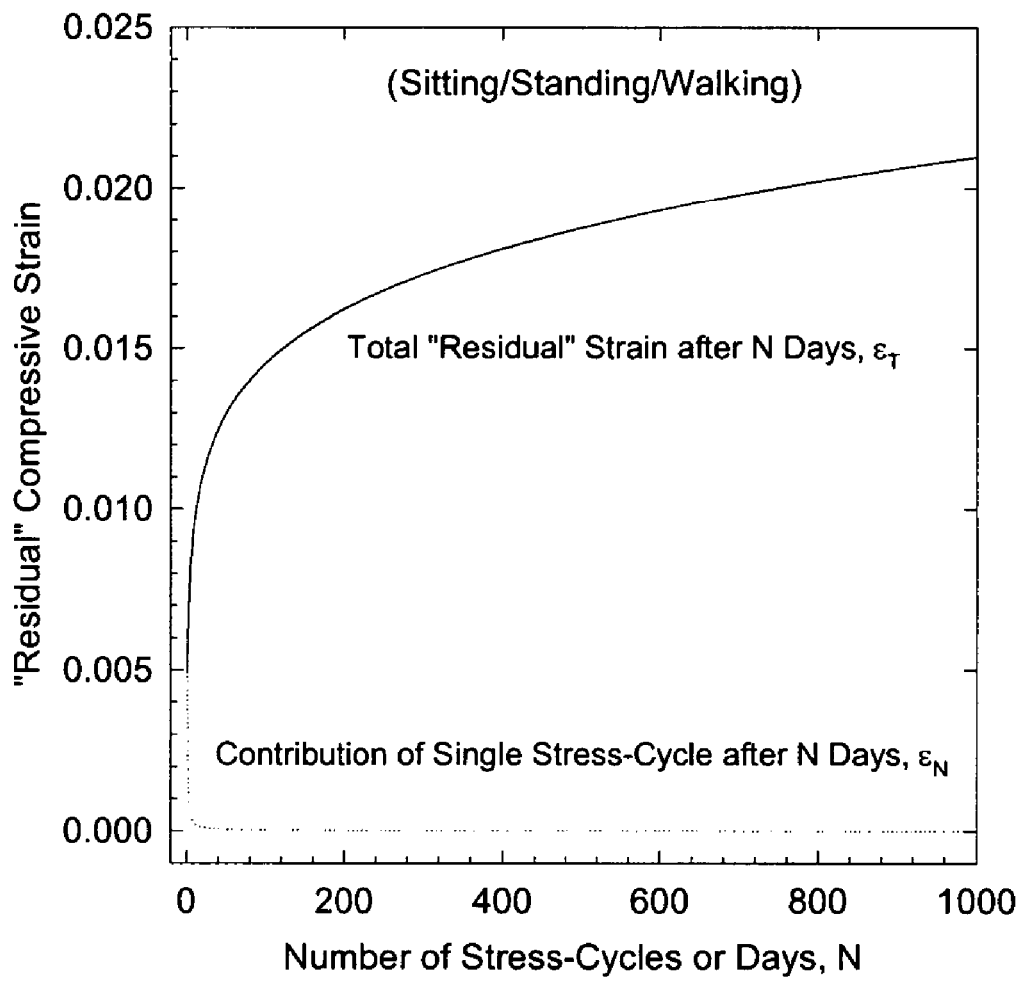
FIG. 9 shows the accumulation of residual strain as a function of number of days or number of stress cycles.

FIG. 9 shows the accumulation of residual strain as a function of number of days or number of stress cycles. Thus for each activity there is a "residual" or accumulated strain contribution. Strain at any time within the cycle can be considered as the sum of the residual strains of each activity (from previous stress cycles) plus the strain resulting from the current stress cycle.

Figure 10:
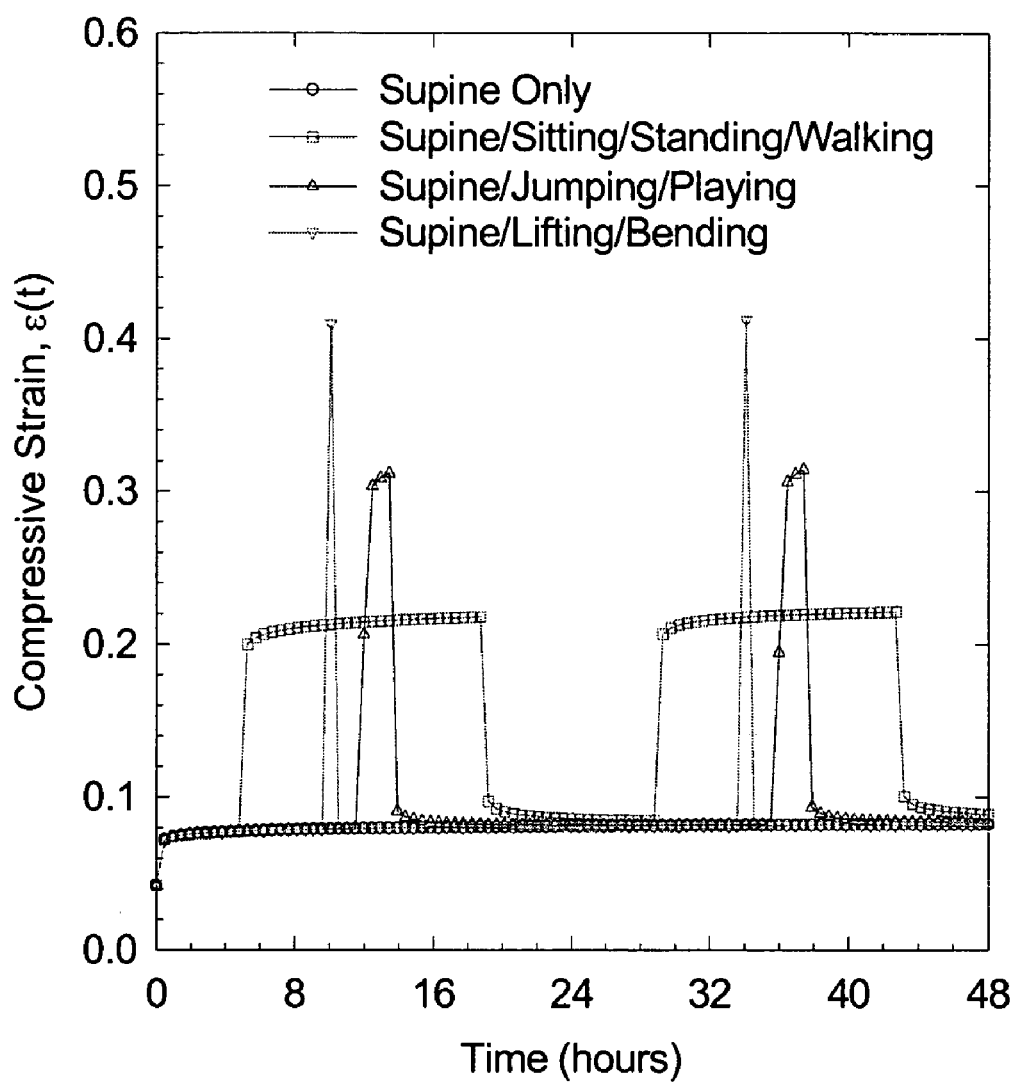
FIG. 10 shows the actual external strain response for each activity for the first two days of the device's predicted in-vivo lifetime.

FIG. 10 shows the actual external strain response for each activity for the first two days of the device's predicted in-vivo lifetime. It should be noted that the activities that are associated with the higher stress levels have the shorter duration. Although the strain during the high stress application is high, the recovery process is relatively rapid after removal of the stress. Activities that have longer times produce larger amounts of "residual" strain.

Figure 11:
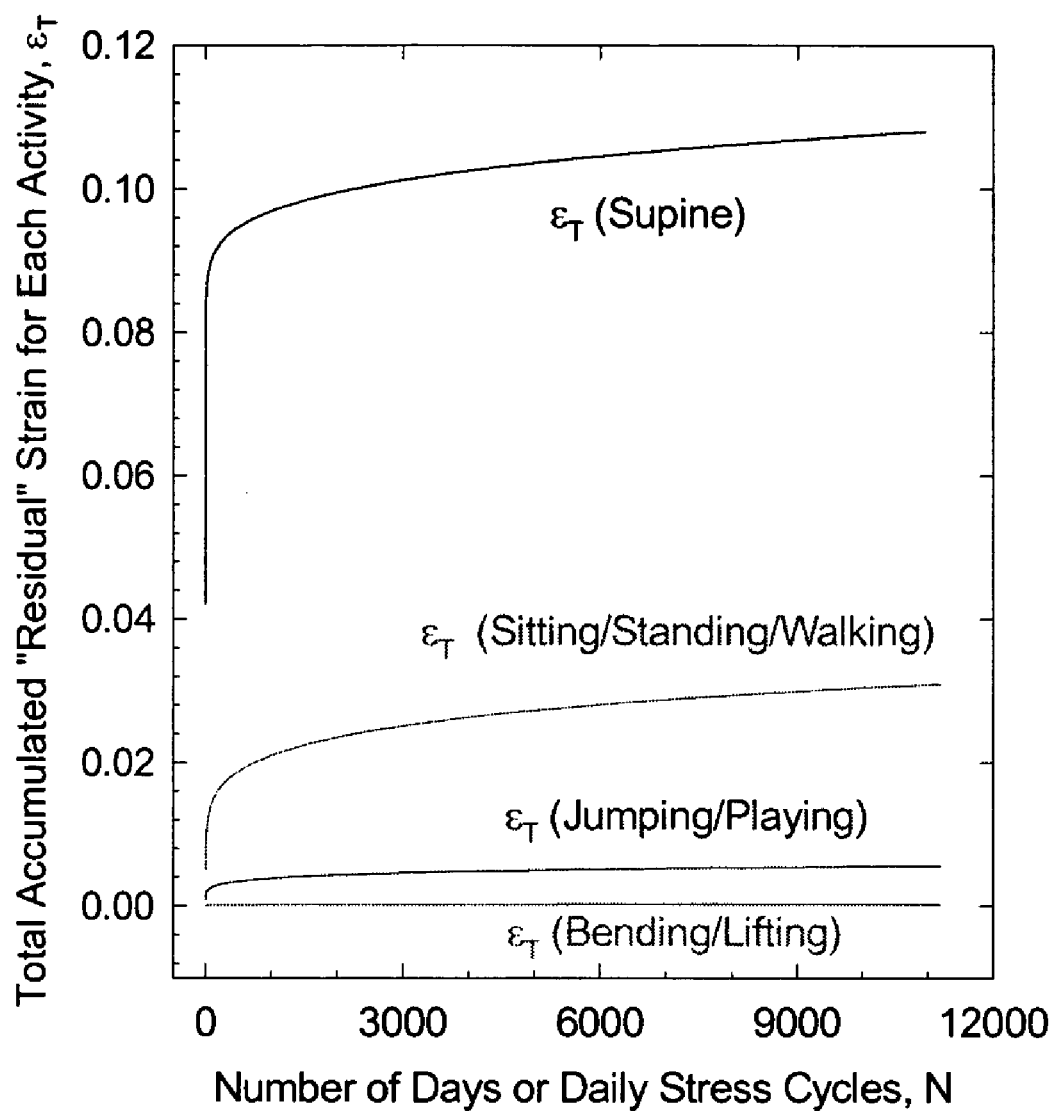
FIG. 11 shows the predicted accumulated "residual" strain for each activity, calculated during a "resting" period (end of day), as a function of number of days into the predicted in-vivo lifetime of the disc device.

FIG. 11 shows the predicted accumulated "residual" strain for each activity, calculated during a "resting" period (end of day), as a function of number of days into the predicted in-vivo lifetime of the disc device. The total strain during resting is the sum of each "residual" strain component for each activity. It is noteworthy that the supine activity is associated with the lowest stress level, but its response contributes to nearly 76% of the total deformation during resting. The bending/lifting activity involves the highest stress levels, but because of its short duration the residual strain from this activity is a negligible component of the total strain during resting. It is also noteworthy that if "microdamage" occurs in the actual application, it is likely caused by the higher-stress-level activity, even if duration is short. This aspect is not included within the present model.

The maximum strain that is produced within the disc during any activity is essentially comprised of the total residual strain for each activity (the strain response to previous activities, i.e. stress history) and the creep deformation caused by the given activity.

Figure 12:
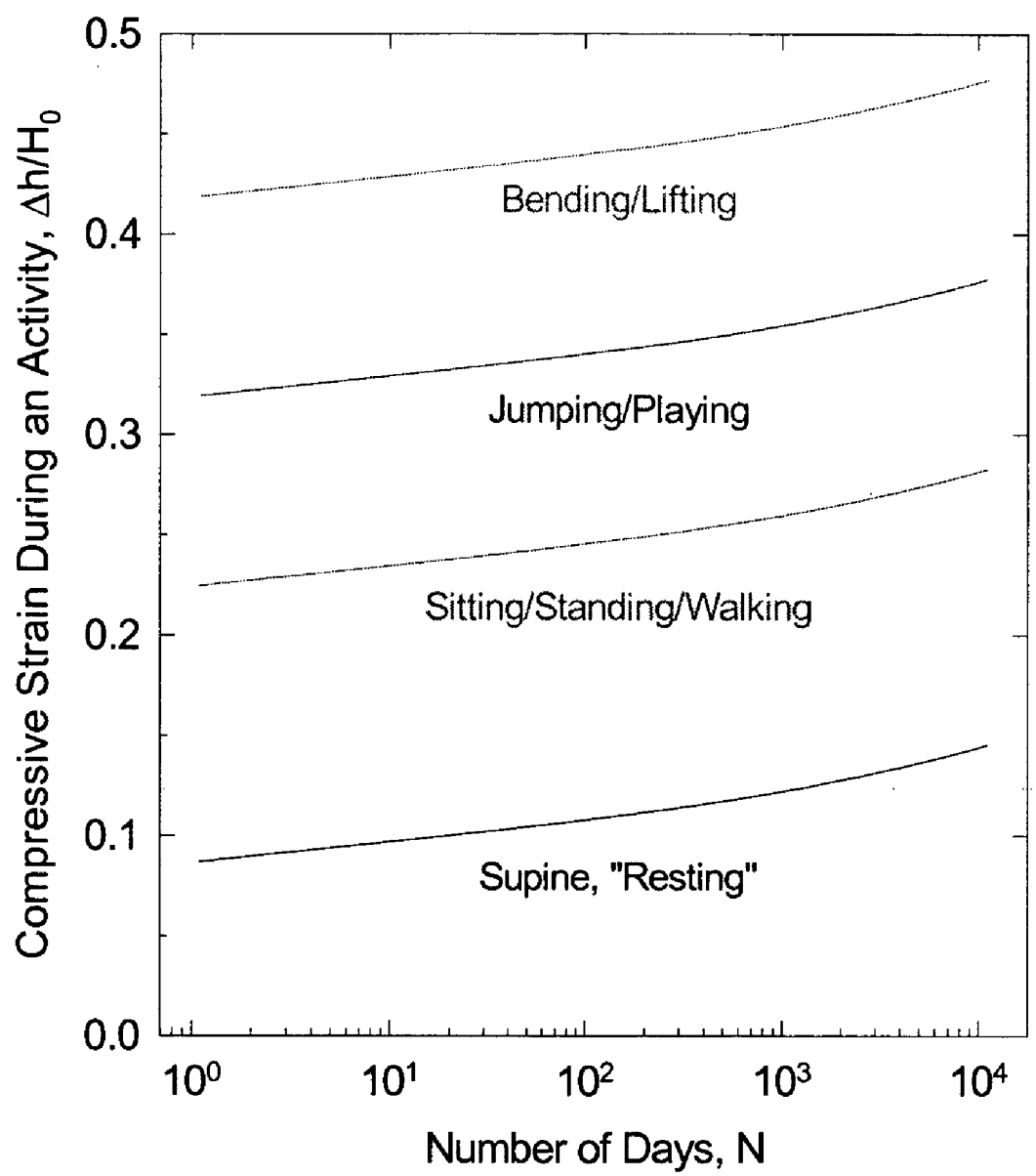
FIG. 12 shows the time-dependent strains of the method of the present invention.

FIG. 12 shows the time-dependent strains that are associated with each of the activities, satisfying the present invention. At this juncture, one can assess and predict external the amount of deflection that will occur in-vivo, within the device as a function of activity-type and the number of days into the device's lifetime. It has been found using the method of the present invention that the disc deflection is related to strain through the original geometry of the device. Based upon the requirements of the device to be used in-vivo, one can assess via external analysis whether the polymer component provides acceptable predictive performance before clinical trials are initiated.

USEFULNESS OF THE INVENTION

The present invention provides viscoelastic property characterization for performance modeling of bio-medical devices that incorporate a polymeric component and are load-bearing during service.

Time-Temperature Superposition can often be used to accelerate testing of pertinent properties. Boltzmann's superposition provides a mathematical methodology for determining the time-dependent strain that develops in response to an imposed stress history. The modeling of the present invention provides an opportunity to describe and predict behavior of the device during in-vivo service as well as it providing a basis for evaluating alternate "candidate" polymers for use in the construction of the device.

The invention is not limited to the above embodiments. The claims follow.

What is claimed is:

1. A method for predicting in-vivo polymer performance in a mammalian body via external experimentation, comprising the steps of:
   (a) determining stress levels and the duration times of stress application, denominated a daily stress cycle that the polymeric component will be subjected to during mammalian body activities for the lifetime of the device;
   (b) determining compressive creep and recoverable creep compliance at selected stresses, as determined in step (a), and temperatures to obtain master curves of compressive creep compliance that analytically define compressive creep strain as functions of time and stress;
   (c) determining single creep/creep recovery strain curves for each mammalian body activity of step (a) calculated from the compressive creep compliance master curves of step (b), wherein a creep phase is interrelated to a recovery phase, to obtain a compressive creep model for a single stress cycle;
   (d) determining a total residual strain after repeated stress cycles from the compressive creep model of step (c), to obtain a compressive creep model for the polymer subjected to repeated daily mammalian activities, denominated compressive stress cycles;
   (e) computing maximum compressive strain curves from a compressive strain during an activity in relation to number of days of activity, wherein the number of days can range from a few days to several years; and
   (f) using the maximum compressive strain curves of step (e) to predict in-vivo performance of the polymer by calculating polymer deflection as a function of original geometry of the device to be made of the polymer.

* * * * *